US009642991B2

(12) United States Patent
Eversull et al.

(10) Patent No.: US 9,642,991 B2
(45) Date of Patent: May 9, 2017

(54) APPARATUS AND METHODS FOR ACCESSING THE LYMPHATIC SYSTEM

(71) Applicants: Christian S. Eversull, Palo Alto, CA (US); Stephen A. Leeflang, Sunnyvale, CA (US); Matthew J. Callaghan, Stanford, CA (US)

(72) Inventors: Christian S. Eversull, Palo Alto, CA (US); Stephen A. Leeflang, Sunnyvale, CA (US); Matthew J. Callaghan, Stanford, CA (US)

(73) Assignee: LXS, LLC, Palo Alto, CA (US)

( * ) Notice: Subject to any disclaimer, the term of this patent is extended or adjusted under 35 U.S.C. 154(b) by 393 days.

(21) Appl. No.: 13/887,277

(22) Filed: May 3, 2013

(65) Prior Publication Data

US 2013/0245607 A1 Sep. 19, 2013

Related U.S. Application Data

(63) Continuation-in-part of application No. 13/100,297, filed on May 3, 2011, now Pat. No. 9,421,316.

(Continued)

(51) Int. Cl.

| | |
|---|---|
| ***A61M 25/10*** | (2013.01) |
| ***A61M 1/34*** | (2006.01) |
| ***A61M 1/36*** | (2006.01) |

(52) U.S. Cl.

CPC .......... *A61M 25/10* (2013.01); *A61M 1/3496* (2013.01); *A61M 1/367* (2013.01);

(Continued)

(58) Field of Classification Search

CPC .............. A61M 25/10; A61M 25/1002; A61M 25/1011; A61M 25/1018;

(Continued)

(56) References Cited

U.S. PATENT DOCUMENTS

| | | | | |
|---|---|---|---|---|
| 4,957,484 | A * | 9/1990 | Murtfeldt | 604/540 |
| 5,300,022 | A | 4/1994 | Klapper et al. | |

(Continued)

FOREIGN PATENT DOCUMENTS

| | | |
|---|---|---|
| WO | 2010080717 A1 | 7/2010 |

OTHER PUBLICATIONS

PCT International Search Report dated Sep. 23, 2013 in International Application No. PCT/US2013/039588 filed May 3, 2013, ISA 210 and 220.

(Continued)

*Primary Examiner* — Bhisma Mehta
*Assistant Examiner* — Hamza Darb

(57) ABSTRACT

Systems and methods are provided for performing a medical procedure within a patient's body that involves a thoracic duct including an ostium communicating with the patient's venous system. A distal end of a catheter is introduced through the patient's venous system into a body lumen adjacent the ostium of the thoracic duct. An expandable member on the distal end of the tubular may be expanded adjacent the ostium, e.g., within the body lumen or the thoracic duct itself, and used to isolate the thoracic duct from the body lumen, whereupon a medical procedure may be performed via the thoracic duct. For example, lymphatic fluid may be removed from the thoracic duct through a lumen of the tubular member and/or one or more agents may be introduced into the thoracic duct through the tubular member.

19 Claims, 7 Drawing Sheets

Related U.S. Application Data

(60) Provisional application No. 61/642,180, filed on May 3, 2012.

(52) U.S. Cl.
CPC ........ *A61M 1/3609* (2014.02); *A61M 1/3653* (2013.01); *A61M 25/1011* (2013.01); *A61M 2202/0405* (2013.01); *A61M 2205/3306* (2013.01); *A61M 2205/3317* (2013.01); *A61M 2230/207* (2013.01); *A61M 2230/208* (2013.01)

(58) Field of Classification Search
CPC .... A61M 2025/1013; A61M 2025/105; A61M 2025/1052; A61M 2025/179; A61M 2202/0405
USPC .......... 604/4.01, 96.01, 101.01, 101.05, 500, 604/508, 509, 510
See application file for complete search history.

(56) References Cited

U.S. PATENT DOCUMENTS

| | | | | |
|---|---|---|---|---|
| 5,766,151 | A | 6/1998 | Valley et al. | |
| 6,443,925 | B1 * | 9/2002 | Schaible | A61L 29/049 604/524 |
| 6,547,775 | B1 | 4/2003 | Blyakhman | |
| 2006/0100658 | A1 | 5/2006 | Obana et al. | |
| 2007/0032754 | A1 | 2/2007 | Walsh | |
| 2007/0255633 | A1 | 11/2007 | Kridel | |
| 2008/0004597 | A1 * | 1/2008 | Lattouf et al. | 604/511 |
| 2008/0140000 | A1 | 6/2008 | Shuros et al. | |
| 2009/0054805 | A1 | 2/2009 | Boyle, Jr. | |
| 2010/0217346 | A1 | 8/2010 | Shuros | |
| 2011/0276023 | A1 | 11/2011 | Leeflang et al. | |
| 2012/0029466 | A1 | 2/2012 | Callaghan et al. | |
| 2012/0330132 | A1 * | 12/2012 | Sorajja et al. | 600/420 |

OTHER PUBLICATIONS

PCT Written Opinion dated Sep. 23, 2013 in International Application No. PCT/US2013/039588 filed May 3, 2013, ISA 237.

Pflug, et al. "The Balves of the Thoracic Duct at the Angulus Venosus" Brit J. Surg, Dec. 1968, vol. 55, No. 12 (6 pages).

* cited by examiner

APPARATUS AND METHODS FOR ACCESSING THE LYMPHATIC SYSTEM

This application is a continuation-in-part of co-pending application Ser. No. 13/100,297, filed May 3, 2011, and also claims benefit of provisional application Ser. No. 61/642,180, filed May 3, 2012, the entire disclosures of which are expressly incorporated by reference herein.

FIELD OF THE INVENTION

The present invention relates generally to apparatus and methods used to perform medical procedures, and, more particularly, to devices, systems, and methods for accessing the lymphatic system of a patient, e.g., to remove, separate, and/or re-infuse lymphatic fluid and/or other components of lymph.

BACKGROUND

The lymphatic system includes a network of vessels generally separate from veins and arteries. Rather than whole blood, the lymphatic vessels carry lymphatic fluid (or lymph). The lymphatic system serves a variety of physiologic purposes, including returning interstitial fluid to the vascular space, transporting fats from the digestive tract, and transporting immune-mediating cells. The composition of lymphatic fluid is similar to plasma. It contains white blood cells, but generally does not contain red blood cells, platelets, or various other components of whole blood. The lymphatic system may be involved in a variety of pathologic states, including lymphatic obstruction leading to lymphedema, leakage of lymphatic fluid, which may lead to chylothorax, or the invasion and spread of malignant cells leading to metastasis. The lymphatic system is involved in nearly any immune mediated response, whether to infectious agents (e.g., viruses, bacteria, parasites, etc.), malignancy, or in the setting of auto-immune disorders. The lymphatic system may serve as a repository for infected cells in disorders such as HIV or may contain a higher concentration of malfunctioning cells in various immune system disorders. To achieve diagnosis and/or treatment of these and other conditions, it may be desirable to access the lymphatic system.

SUMMARY

The present invention is directed generally to apparatus, systems, and methods for performing medical procedures, and, more particularly, to apparatus, systems, and methods for accessing the lymphatic system of a patient, e.g., to remove, separate, and/or re-infuse lymphatic fluid.

Historically, the lymphatic vessels have been accessed rarely, generally by direct approach. For example, some diagnostic procedures involve direct cannulation of peripheral lymphatic vessels, e.g., to infuse dye for identification of lymph nodes. Direct access of the central lymphatic vessels, such as the thoracic duct, is generally avoided. A defect, for example, in the thoracic duct generally does not readily close on its own, leading to significantly morbid conditions, such as chylothorax (persistent collection of lymphatic fluid around the lungs).

The lymphatic system does, however, eventually drain into the vasculature. A majority of lymphatic vessels come to a confluence in the thoracic duct which generally enters the venous system at the junction of the left subclavian vein and the left internal jugular vein. A series of valves generally facilitate one-way flow of lymphatic fluid into the venous system and prevent reflux of whole blood into the thoracic duct. Although not well studied, disruption of one or more of these valves may have negative consequences. Therefore, it may be desirable to protect these valves and/or the lymphatic vessels themselves from damage.

Given the location of the thoracic duct, it may be feasible and desirable to access the lymphatic system by isolating or cannulating the thoracic duct via the venous system. Accessing the lymphatic vessels and removing and processing lymphatic fluid may be achieved using specialized catheter-based systems, as described elsewhere herein. Venous access may be achieved from any suitable location, including the left or right internal or external jugular, subclavian, axillary, anterior cubital, or femoral veins. Navigation to the thoracic duct may be aided by ultrasound, fluoroscopy, direct visualization, MRI, CT, and/or other imaging.

When accessing the lymphatic system trans-venously, it may be desirable to substantially isolate the thoracic duct or other lymphatic vessel, e.g., in order to selectively remove lymphatic fluid without removing significant amounts of whole blood, and/or to introduce fluids, agents, and the like selectively into the lymphatic vessels. It may also be desirable to selectively remove a portion of lymphatic fluid that is unneeded or pathologic and re-infuse the remaining portion back into the body.

Potential clinical applications may include drainage of lymphatic fluid for treatment of volume overload, for example, in the setting of congestive heart failure, depletion of lymphocytes or other immune system constituents, for example, in the setting of auto-immune disorders, preparation for transplantation procedures, treatment of infections residing primarily in immune-mediating cells, decompression of the lymphatic system to facilitate closure of leaking lymphatic vessels, treatment of lymphatic obstruction, and/or to otherwise remove fluid volume or pathologic constituents of lymphatic fluid. Further clinical applications may include diagnosis and/or monitoring of malignancy or metastatic spread of malignant cells, or treatment of infection or malignancy, for example, by infusion of antibiotic, antiviral, antiparisitic, and/or chemotherapeutic agents directly into the lymphatic system. Other applications may include rapid immunization by direct introduction of antigens and/or antigenic material into the lymphatic system, or other applications where sampling or removal of lymphatic fluid or infusion of diagnostic or therapeutic agents is beneficial.

In accordance with an exemplary embodiment, an apparatus is provided for accessing a thoracic duct of a patient's body that includes a tubular member comprising a flexible, substantially straight proximal portion and a flexible, curved distal portion, wherein the proximal portion has a first length and a first outer diameter, and the distal portion has a second length and a second outer diameter, the second length shorter than the first length and the second outer diameter is smaller than the first outer diameter; and a balloon on the distal portion adjacent a distal tip thereof, the balloon sized for substantially isolating the thoracic duct when expanded therein.

In accordance with still another embodiment, an apparatus is provided for accessing a thoracic duct of a patient's body that includes a tubular member comprising a flexible, substantially straight proximal portion sized for introduction into a vein and a flexible, curved distal portion sized for introduction into a thoracic duct, and an aspiration lumen extending from a proximal end of the proximal portion to one or more inlet ports on a distal tip of the distal portion; and an expandable member on the distal portion adjacent the distal tip, the expandable member expandable from a collapsed configuration to allow introduction into a thoracic duct and an expandable configuration for substantially isolating the thoracic duct when expanded therein. In addition, the distal portion and the proximal portion may have one or more of the following: a) wherein the proximal portion has a first length and the distal portion has a second length, the second length shorter than the first length; b) wherein the proximal portion has a first outer diameter, and the distal portion has a second outer diameter, the second outer diameter is smaller than the first outer diameter; c) wherein the distal portion has greater flexibility than the proximal portion; d) wherein the distal portion is formed from softer materials than the proximal portion; and e) wherein the aspiration lumen has a first inner cross-section in the proximal portion and a second inner cross-section in the distal portion, the second cross-section smaller than the first inner cross-section.

In accordance with yet another embodiment, a method is provided for accessing a thoracic duct of a patient's body that includes providing a tubular member comprising a proximal portion and a flexible distal portion having a curvilinear shape in a relaxed state and terminating in a distal tip, the distal portion having a smaller outer diameter than the proximal portion; introducing the tubular member into a patient's vasculature via a percutaneous access site in the patient's left internal jugular vein; advancing the tubular member until the distal portion is disposed within a junction of the left internal jugular vein and the patient's left subclavian vein and the proximal portion is disposed through the access site and in the left internal jugular vein; manipulating the tubular member to orient the distal tip towards the thoracic duct; retracting the tubular member to direct the distal tip into the thoracic duct beyond a terminal valve of the thoracic duct; and expanding an expandable member on the distal portion adjacent the distal tip within the thoracic duct beyond the terminal valve to substantially isolate the thoracic duct from the left internal jugular vein and left subclavian vein.

In accordance with still another embodiment, a method is provided for accessing a thoracic duct of a patient's body that includes providing a tubular member comprising a proximal portion and a flexible distal portion having a curvilinear shape in a relaxed state and terminating in a distal tip, the distal portion having a smaller outer diameter than the proximal portion; introducing the tubular member into a patient's vasculature; advancing the tubular member until the distal portion is disposed within a junction of the left internal jugular vein and the patient's left subclavian vein; manipulating the tubular member to orient the distal tip towards the thoracic duct; retracting the tubular member to direct the distal tip into the thoracic duct beyond a terminal valve of the thoracic duct; and expanding an expandable member on the distal portion adjacent the distal tip within the thoracic duct beyond the terminal valve to substantially isolate the thoracic duct from the left internal jugular vein and left subclavian vein.

In accordance with another embodiment, a method is provided for performing a medical procedure within a patient's body, the body comprising a thoracic duct including an ostium communicating with the patient's venous system that includes introducing a distal portion of a tubular member through the patient's venous system into a body lumen adjacent the ostium of the thoracic duct, the distal portion biased to a curvilinear configuration; manipulating the tubular member until a distal tip of the distal portion enters the ostium of the thoracic duct; retracting the tubular member to direct the distal portion into the thoracic duct until an expandable member on the distal portion passes through a terminal valve of the thoracic duct; expanding the expandable member within the thoracic duct beyond the terminal valve to substantially isolate the thoracic duct from the body lumen; and performing a medical procedure via the thoracic duct.

In accordance with yet another embodiment, a system is provided for performing a medical procedure via a thoracic duct of a patient's body that includes a catheter or other tubular member including a proximal end, a distal end sized for introduction into a body lumen, and an aspiration lumen extending from the proximal end to a port in the distal end. An expandable member may be provided on the distal end, e.g., sized and/or shaped for substantially isolating the thoracic duct when expanded within the body lumen or thoracic duct itself. One or more external components may be coupled to the proximal end of the tubular member, e.g., a source of vacuum for removing fluid within the body lumen via the port and aspiration lumen, a detector for analyzing the fluid removed from the body lumen to identify lymphatic fluid, a separator for separating the lymphatic fluid or components of the lymphatic fluid from other fluid in the fluid removed from the body lumen, and/or a container for collecting the lymphatic fluid or components of the lymphatic fluid separated from other fluid.

In accordance with another embodiment, a method is provided for performing a medical procedure within a patient's body that includes a thoracic duct including an ostium communicating with the patient's venous system. A distal end of a tubular member may be introduced through the patient's venous system into a body lumen adjacent the ostium of the thoracic duct. An expandable member on the distal end of the tubular member may be expanded adjacent the ostium, e.g., within the body lumen or the thoracic duct itself, and used to substantially isolate the thoracic duct from the body lumen, whereupon a medical procedure may be performed via the thoracic duct. For example, lymphatic fluid may be removed from the thoracic duct through a lumen of the tubular member and/or one or more agents may be introduced into the thoracic duct through the tubular member.

In an exemplary embodiment, fluid may be removed from the patient's body through a lumen of the tubular member, and the removed fluid may be analyzed to determine whether the fluid comprises lymphatic fluid or blood. For example, if the fluid comprises blood, the thoracic duct may not be isolated from the body lumen, and the removal of fluid may be stopped and/or the fluid may be directed to a waste container. If the fluid is lymphatic fluid, the fluid may be directed to a storage container, or components of the lymphatic fluid may be separated from other components of the fluid, and the separated components may be directed to a storage container. Optionally, the stored lymphatic fluid or the separated components of the lymphatic fluid may be infused back into the patient's body, if desired.

Other aspects and features of the need for and use of the present invention will become apparent from consideration of the following description taken in conjunction with the accompanying drawings.

BRIEF DESCRIPTION OF THE DRAWINGS

It will be appreciated that the exemplary apparatus shown in the drawings are not necessarily drawn to scale, with emphasis instead being placed on illustrating the various aspects and features of the illustrated embodiments. The drawings illustrate exemplary embodiments of the invention, in which.

DETAILED DESCRIPTION OF THE EXEMPLARY EMBODIMENTS

Figure 1:
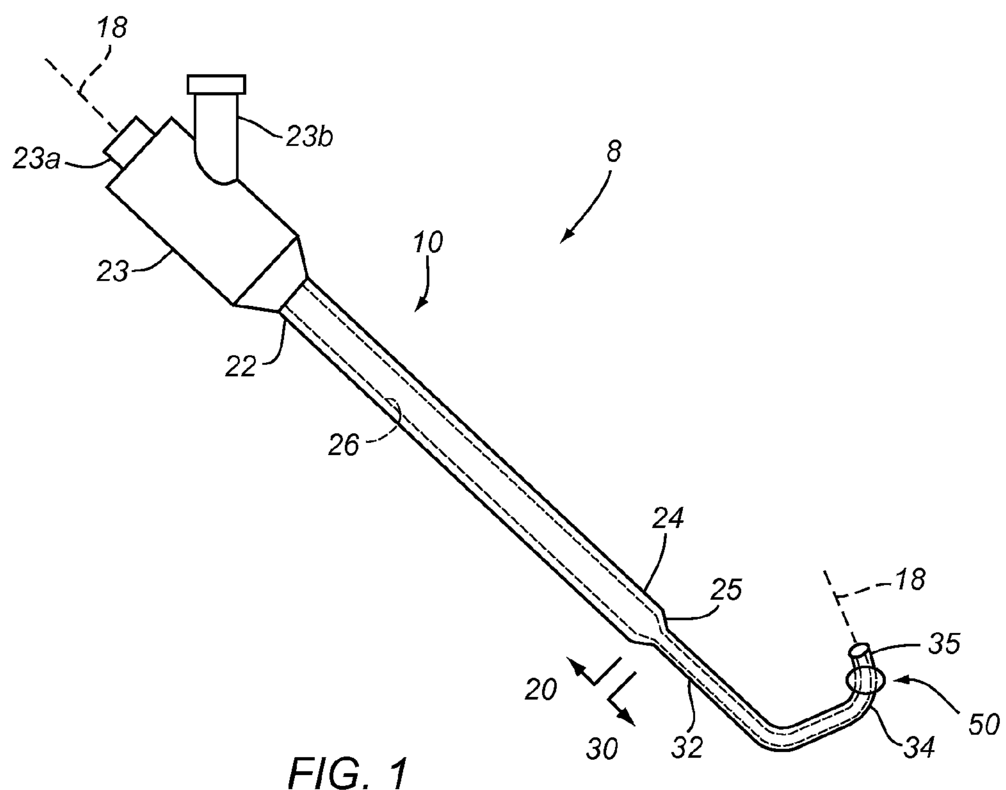
FIG. 1 is a perspective view of an exemplary embodiment of an apparatus for accessing a thoracic duct.
Figure 2A:
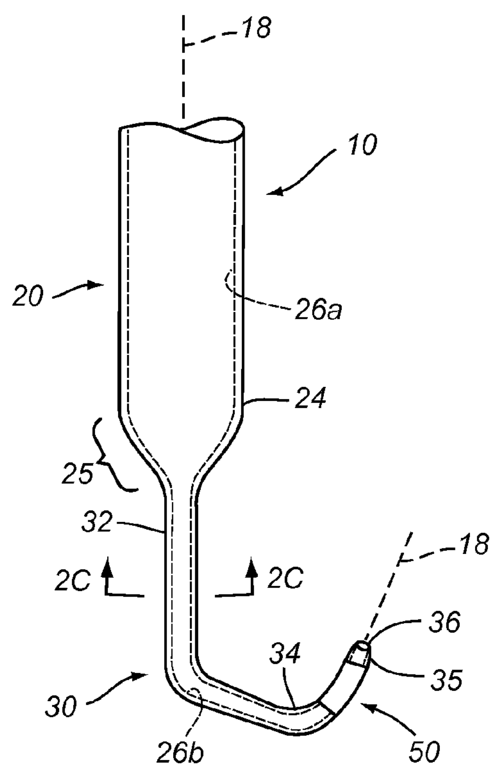
FIGS. 2A and 2B are details of a distal portion of the apparatus of FIG. 1, showing a balloon on the distal portion in collapsed and enlarged configurations, respectively.
Figure 2B:
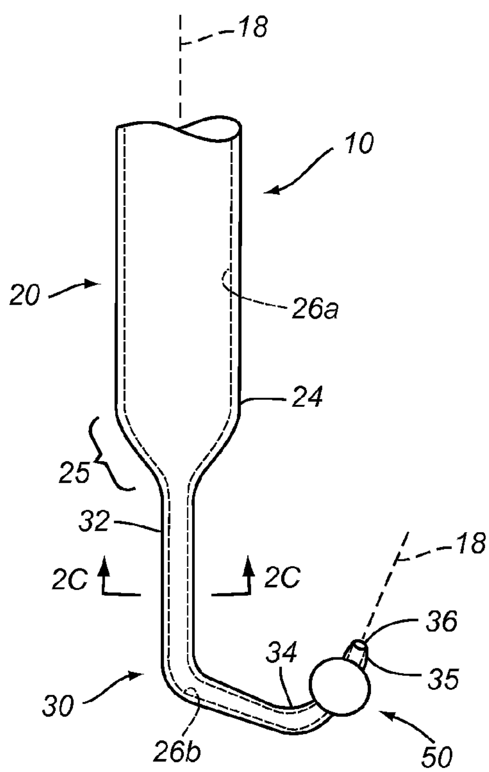

Turning to the drawings, FIGS. 1-2B show an exemplary embodiment of an apparatus 8 for accessing and/or isolating the lymphatic system of a patient 90 (not shown, see, e.g., FIG. 5 for anatomical references), e.g., to aspirate or otherwise draw lymphatic fluid from the thoracic duct 94, as described further below. Generally, the apparatus 8 includes a catheter or other tubular member 10 including a proximal or main portion 20, e.g., sized and/or shaped for introduction into a blood vessel of the patient, such as a jugular vein 92*b* (not shown, see FIG. 5), and a relatively smaller distal portion 30, e.g., sized and/or shaped for introduction into a thoracic duct 94 of the patient 90 (also not shown, see FIG. 5), thereby defining a central longitudinal axis 18 for the apparatus 8.

A balloon or other expandable member 50 may be provided on the distal portion 30, e.g., sized for introduction into a thoracic duct in a collapsed configuration and expandable to an enlarged configuration for substantially sealing and/or isolating the thoracic duct 94, as described further below. The balloon 50 may be formed from elastic material, e.g., such that the balloon 50 may be inflated to multiple diameters to accommodate engaging the wall of thoracic ducts of various sizes and/or shapes, to provide a substantially fluid-tight seal without applying excessive forces against the wall.

Figure 5:
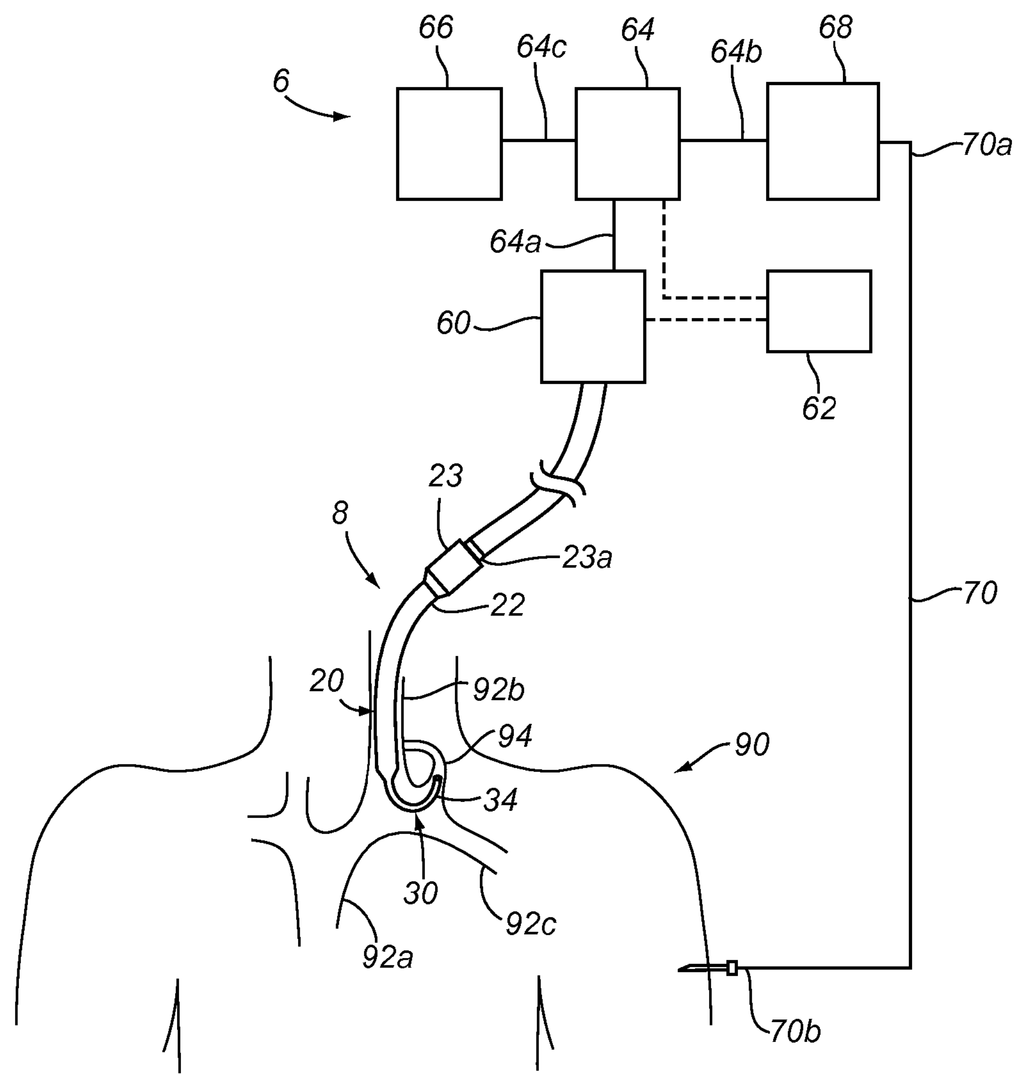
FIG. 5 is a detail of a patient's body showing a schematic of an exemplary system for accessing the lymphatic system of the patient including an apparatus, such as that shown in FIGS. 1-2B.

Generally, the proximal and distal portions 20, 30 of the catheter 10 have different dimensions and/or properties. For example, the proximal portion 20 may have a substantially straight shape in a relaxed state, yet may be sufficiently flexible to be introduced into a patient's body 90, e.g., sufficiently flexible to be introduced into the venous system from a percutaneous access site, such as via a left or right internal or external jugular vein, subclavian vein, axillary vein, or other percutaneous access site. In an exemplary embodiment, access may be gained from the left internal jugular vein 92*b* to approach the junction of the left internal jugular vein 92*b* and left subclavian vein 92*c*, as shown in FIG. 5. The distal portion 30 may have a curvilinear shape in a relaxed state, e.g., a simple curved shape or a more complicated shape including one or more curved and/or straight sections, which may facilitate introduction of the distal portion 30 into the thoracic duct 94, e.g., from the jugular vein 92*b*, as described further below.

In addition or alternatively, the proximal portion 20 may be substantially longer than the distal portion 30, e.g., to allow the proximal portion 20 to be introduced into the patient's body from an access site, e.g., into the left internal jugular vein 92*b*, and manipulated to introduce the distal portion 30 into the thoracic duct 94. For example, as shown in FIG. 1, the proximal portion 20 may include a proximal end 22 including a handle or hub 23, and a distal end 24 coupled or otherwise including a transition 25 to the distal portion 30. In exemplary embodiments, the proximal portion 20 may have a length from the handle 23 to the transition 25 between about three and one hundred twenty centimeters (3.0-120 cm), or alternatively between about three and thirty centimeters (3.0-30.0 cm), and may have an outer diameter or other maximum cross-section between about one and seven millimeters (1.0-7.0 mm), or alternatively between about one and three millimeters (1.0-3.0 mm).

The transition 25 may include a tapered shape, as shown, an abrupt step-down shape (not shown), and the like to transition between the proximal and distal portions 20, 30. If the proximal and distal portions 20, 30 are formed from different materials, the transition 25 may connect the different materials together, e.g., by bonding with adhesive, fusing, sonic welding, heat forming, and the like.

The distal portion 30 may have a proximal end 32 extending distally from the transition 25, e.g., aligned substantially axially with the proximal portion 20, and a distal end 34 terminating in a distal tip 35. In exemplary embodiments, the distal portion 30 may have a length from the proximal end 32 to the distal tip 35 between about one and ten centimeters (1.0-10.0 cm), and may have an outer diameter or other maximum cross-section between about half to five millimeters (0.5-5.0 mm), or alternatively between about half and two millimeters (0.5-2.0 mm). Thus, the distal portion 30 may be substantially shorter than the proximal portion 20, e.g., such that the proximal portion 20 may extend from a percutaneous access site (not shown) into the junction of the left internal jugular vein 92*b* and the left subclavian vein 92*c*, and the distal portion 30 may simply curve and enter the thoracic duct 94, as described further elsewhere herein.

The distal portion 30 may have a substantially uniform outer diameter between the proximal end 32 and the distal tip 35, or the diameter may vary, e.g., tapering at or adjacent the distal tip 35 to provide a substantially atraumatic distal tip 35.

In addition, the distal portion 30 may have a flexibility greater than the proximal portion 20. For example, the proximal portion 20 may have sufficient column strength, stiffness, torque, and the like such that the proximal portion 20 may be manipulated from the handle 23 without substantial risk of the distal end 24 of the proximal portion 20 buckling or kinking, while providing sufficient flexibility to accommodate introduction into curved vessels within the patient's body. In exemplary embodiments, the proximal portion 20 may have a substantially rigid or semi-rigid proximal end 22, e.g., to facilitate advancement of the distal portion from the handle 23, while the distal end 24 may be semi-rigid or flexible. Moreover, the device properties may be optimized to responsively translate manipulation of the proximal end 22 into movement of the distal portion 30, e.g. by means of rotation, torque, angular manipulation, withdrawal, and/or advancement.

The distal portion 30 may be substantially flexible, e.g., biased to the curvilinear shape when free from external forces, yet flexible to accommodate bending, compressing (of the distal tip 35 towards the proximal portion 20), and/or other movement of the distal portion 30 to facilitate introducing the distal tip 35 into the thoracic duct. In exemplary embodiments, the distal portion 30 may be formed from PEBAX, urethane, silicone, and/or other soft and/or flexible materials, e.g., having substantially uniform properties along the length of the distal portion 30, or becoming progressively (or otherwise) softer and/or more flexible from the proximal end 32 to the distal tip 35. The proximal and distal portions 20, 30 may be formed from different materials to provide the desired flexibility. For example, the proximal portion 20 may include a reinforcement layer, e.g., braiding and the like between inner and outer layers (not shown), while the distal portion 30 may simply include a single layer or vice versa. Alternatively, a different reinforcing layer (e.g. braid, coil, stent-like structure or other scaffolding) may be used in the proximal and distal portions 20, 30.

In addition or alternatively, relative flexibility may be obtained by providing different wall thicknesses, e.g., from the same or different materials. For example, as shown in FIGS. 2A and 2B, the proximal portion 20 may have a relatively larger wall thickness than the distal portion 30, which may enhance relative flexibility of the distal portion 30. In exemplary embodiments, the wall thickness of the proximal portion 20 may be between about 0.1 and three millimeters (0.1-3.0 mm), while the wall thickness of the distal portion 30 may be between about 0.1 and two millimeters (0.1-2.0 mm).

As shown in FIG. 1, the distal portion 30 may include multiple substantially straight sections between curved sections, e.g., to provide a "hook" shape having an overall angle of curvature equal to or greater than ninety degrees, e.g., between about ninety and three hundred sixty degrees (90-360°), or between about ninety and one hundred fifty degrees (90-150°). Such radii of curvature may facilitate introduction into the thoracic duct 94, which may connect near the junction of the jugular, subclavian, and brachiocephalic veins 92 at an acute angle, such that a radius of curvature greater than ninety degrees (90°) may be necessary to align the distal tip 35 with the thoracic duct 94 when the proximal portion 20 is within the left internal jugular vein 92*b*, as described further elsewhere herein.

Figure 3A:
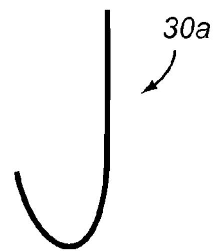
FIGS. 3A-3C are schematic views showing alternative relaxed shapes for the distal portion of an apparatus, such as that shown in FIG. 1.
Figure 3B:
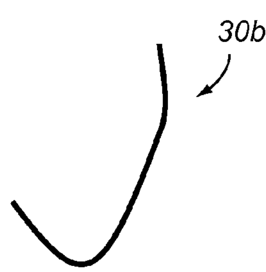
Figure 3C:
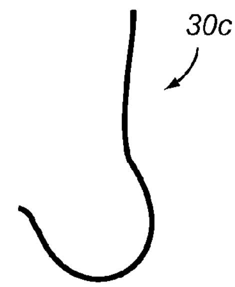

In an alternative embodiment, shown in FIG. 3A, the distal portion 30*a* may include a single substantially continuous radius of curvature approaching one hundred eighty degrees (180°). In a further alternative, shown in FIG. 3B, the distal portion 30*b* may have a more complicated curvilinear shape, e.g., including a first straight section between a bend and a radiused section ending in a substantially straight distal tip (which may carry a balloon, not shown). In yet another alternative, shown in FIG. 3C, the distal portion 30*c* may include a continuous curved shape including a first bend in an opposite direction to the main radius of curvature of the distal portion 30*c*. Such shapes may orient the distal tip 35 of the catheter 10 back towards the proximal end 22 with the distal tip 35 defining a desired angle relative to the longitudinal axis 18 within the proximal portion 20.

In still another alternative, the distal portion 30 may include a curved section of constant or variable radius having an arc angle of between about zero and three hundred sixty degrees (0°-360°) and a radius of curvature between about one and fifteen millimeters (1.0-15.0 mm). Further alternatively, the distal portion 30 may include one or more discrete bends, creating a distal shape having a width between about two and thirty millimeters (2.0-30.0 mm). More generally, any of the foregoing shapes may be optimized to locate the distal tip 35 at or near the thoracic duct ostium and simultaneously align the tip vector with the entry vector of the thoracic duct 94. Furthermore, the shape of the distal portion 30 may be sufficiently resilient to return to its pre-set shape, e.g. after introduction through a sheath, repeated manipulation, and the like.

Optionally, the distal portion 30 may include one or more features to facilitate identification and/or localization of the distal portion 30, e.g., the balloon 50 and/or distal tip 35, within a patient's body using external imaging. For example, one or more echogenic features, may be provided on or in the wall of the balloon 50 and/or on the distal tip 35, which may facilitate monitoring the distal portion 30 using ultrasound imaging. Such exemplary features may include doping or coating with tungsten, tungsten carbide, titanium dioxide, iron oxide, zinc oxide, platinum, gold, barium, bismuth, and/or titanium; echogenic surface modifications such as reflective gratings, surface depression and/or projections; inclusions, for example, of glass particles, air bubbles, and the like, including those described in U.S. Pat. No. 5,921,933, the entire disclosure of which is expressly incorporated by reference herein. Alternatively, radiopaque and/or other markers (also not shown) may be provided to facilitate monitoring the distal portion 30 using fluoroscopy or other external imaging.

Returning to FIGS. 1-2B, the catheter 10 may include one or more lumens 26, 27 extending therethrough, e.g., from the proximal end 22 of the proximal portion 20 to the distal portion 30. For example, as shown in FIG. 1, an aspiration or infusion lumen 26 may be provided that communicates with a port 23*a* in the handle 23 and extends through the entire proximal and distal portions 20, 30 to one or more inlet (or outlet) ports 36 adjacent the distal tip 35. As best seen in FIGS. 2A and 2B, the aspiration lumen 26 may include a relatively large region 26*a* within the proximal portion 20 and a relatively small region 26*b* within the distal portion 30. In exemplary embodiments, the proximal region 26*a* of the lumen 26 may have an inner diameter (or other maximum cross-section) between about one and five millimeters (1.0-5.0 mm), while the distal region 26*b* may have an inner diameter (or other maximum cross-section) between about 0.1 and three millimeters (0.1-3.0 mm).

The smaller diameter of the distal region 26*b* may allow the outer diameter of the distal portion 30 to be minimized, e.g., to provide desired flexibility and/or minimize the size of the distal portion 30 to facilitate introduction into the thoracic duct 94, while the larger diameter of the proximal region 26*a* may allow lymph or other fluids to be drawn through the catheter 10 more easily. For example, the larger diameter over most of the length of the catheter 10 may expose the fluid to lower friction, which may increase flow rate and/or reduce the risk of lysing or otherwise damaging cells or other components of the fluid being aspirated or delivered through the lumen 26 of the catheter 10.

Figure 4A:
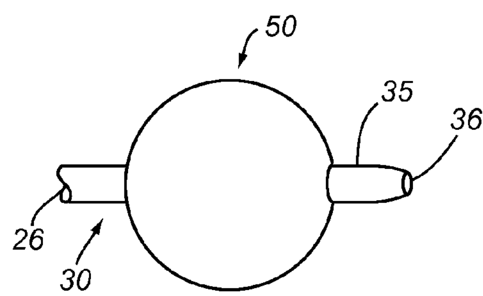
FIGS. 4A-4C are details of alternative embodiments of distal tips that may be provided on an apparatus, such as that shown in FIGS. 1-2B.
Figure 4B:
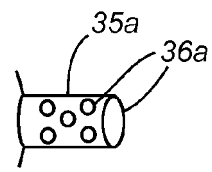

As shown in FIGS. 2A, 2B, and 4A, the aspiration lumen 26 may communicate with a single inlet port 36 in the distal tip 35, e.g., aligned with the central longitudinal axis 18. Alternatively, multiple inlet ports may be provided on the distal tip, e.g., to reduce the risk of a single or multiple ports becoming occluded with fluid or debris and/or contacting and sucking the wall of the thoracic duct or other body lumen against the distal tip 35, which may otherwise prevent fluid from being drawn into the lumen 26. For example, as shown in FIG. 4B, the distal tip 35*a* may include a plurality of side ports in addition to the axial inlet port 36*a*, or, as shown in FIG. 4C, one or more slots (two shown) may be provided that extend partially from the axial inlet port 36*b*.

Figure 2C:
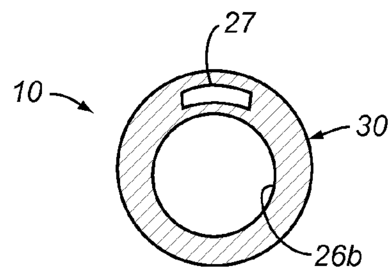
FIG. 2C is a cross-section of the distal portion of the apparatus of FIGS. 2A-2B taken along line 2C-2C.

In addition, turning to FIG. 2C, the catheter 10 may include an inflation lumen 27, e.g., extending through the proximal and distal portions 20, 30 and communicating with an interior of the balloon 50. The inflation lumen 27 may communicate with a port 23*b* on the handle 23, shown in FIG. 1, which may allow a source of inflation and/or vacuum, e.g., a syringe and the like (not shown), to be coupled to the catheter 10 and communicate with the interior of the balloon 50, e.g. to allow the balloon 50 to be inflated and collapsed, as described elsewhere herein. Alternatively, another expanded member, e.g., a mechanically expandable frame and the like (not shown, see, e.g., FIGS. 9A-9C), may be provided on the distal portion 30 instead of the balloon 30. In this alternative, a mechanical actuator, e.g., a slider, wheel, and the like (also not shown, may be provided on the handle 23 that is coupled to the frame or other expandable member for directing the expandable member between collapsed and enlarged configurations.

Optionally, the catheter 10 may include one or more additional lumens, if desired. For example, an infusion lumen (not shown) separate from the aspiration lumen 26 may be provided, which may allow infusion of fluids or agents through the catheter 10 to one or more outlets (also not shown) on the distal portion 30, independent of aspiration or removal of fluid through the lumen 26. Infusion of fluids may be into the thoracic duct 94 or into the vein(s) at any point along the course of the catheter 10. Infused fluids may include at least some part or all of fluids aspirated by means of the same catheter. In addition, a guidewire lumen and/or a stylet lumen (not shown) may be provided that extends through the proximal portion 20 into the distal portion 30, e.g., for at least partially straightening and/or supporting the distal portion 30 during introduction into a patient's body, as described elsewhere herein.

Figure 6:
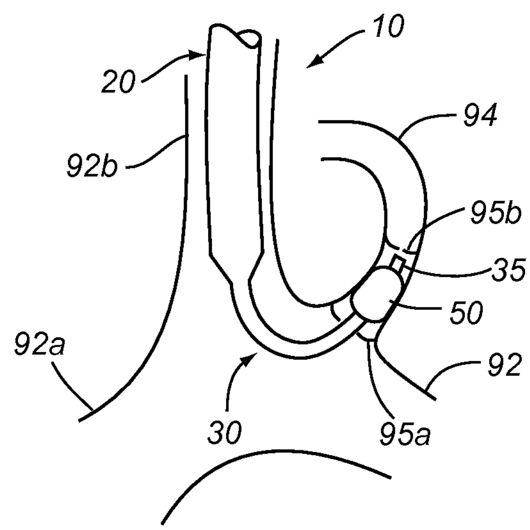
FIG. 6 is a detail of a patient's body, showing the distal portion of a catheter positioned within a thoracic duct of the patient and with a balloon thereon inflated to substantially isolate the thoracic duct from the patients venous system.

Turning to FIGS. 5 and 6, the apparatus 8 may be used to perform a medical procedure within the patient's body 90 that includes accessing the thoracic duct 94, which may be related to any of the conditions and/or treatments described elsewhere herein. Initially, the catheter 10 may be introduced into the patient's body 90, e.g., into the venous system from a percutaneous access site, such as the left or right internal or external jugular, subclavian, axillary, anterior cubital, or femoral veins.

To facilitate introduction and/or navigation of the catheter 10, one or more other devices may be used in conjunction with the catheter 10, if desired. For example, in one embodiment, a guidewire (not shown) may be introduced and advanced from the percutaneous access site, through any intervening vessels into the junction of the left internal jugular vein 92*b* and left subclavian vein 92*c*, and into the thoracic duct 94. The guidewire may be backloaded into the inlet port 36 of the distal portion 30 and through the aspiration lumen 26 (or through a separate lumen, e.g., a dedicated guidewire lumen, not shown, if provided on the catheter 10). The catheter 10 may then be advanced over the guidewire into the access site and intervening vessels, and at least the distal tip 35 of the distal portion 30 may be introduced into the thoracic duct 94.

In addition or alternatively, other devices may be used to at least partially straighten and/or otherwise support the distal portion 30 of the catheter 10. For example, a stylet (not shown) may be positioned within the catheter 10, e.g., within the aspiration lumen 26 or a separate lumen (not shown) such that the stylet enters at least partially into the distal portion 30, thereby directing the distal portion 30 from its relaxed curvilinear shape to a less curved or substantially straight configuration (not shown) and/or otherwise supporting the distal portion 30 from buckling or kinking. The distal portion 30 may then be introduced through the access site and any intervening vessels until the distal tip 35 is located adjacent the thoracic duct 94, e.g., within the junction of the jugular and subclavian veins 92*b*, 92*c*. The stylet may be sufficiently flexible to accommodate introducing the distal portion 30 through any bends or tortuous anatomy encountered between the access site and the thoracic duct 94. Once the distal tip 35 is located adjacent the thoracic duct 94, e.g., within the junction of the left internal jugular vein 92*b* and the left subclavian vein 92*b*, the stylet may be removed, thereby allowing the distal portion 30 to return towards its relaxed, curvilinear configuration. Alternatively, one or more shaped stylets may be used to accentuate, alter, essentially create the shape of the distal portion 30. Further, a stylet may be used to direct the distal portion 30 toward and/or into the thoracic duct 94, e.g., by independent and/or co-manipulation (e.g. twisting, advancing, retracting) of the stylet and the catheter 10.

In another alternative, a sleeve, sheath, cover, and the like (also not shown) may be provided over the catheter 10 until the distal portion 30 is sufficiently covered, e.g., to at least partially straighten and/or support the distal portion 30. The distal portion 30 may then introduced into the patient's body 90 until the distal tip 35 is disposed adjacent the thoracic duct 94, whereupon the cover may be removed to expose and release the distal portion 30, again thereby allowing the distal portion 30 to return towards its relaxed, curvilinear configuration.

With the distal portion released or exposed within the junction, the proximal portion 20 of the catheter 10 may then be manipulated, e.g., advanced and/or retracted, rotated, and the like until the distal tip 35 enters the thoracic duct 94, as shown in FIG. 5. For example, without a guidewire, the catheter 10 may be manipulated until the distal portion 30 "hooks" the ostium of the thoracic duct 94. Because of the soft and/or flexible nature of the distal portion 30, such manipulation may be completed without substantial risk of perforation or other damage to the vessels. In addition, given that the thoracic duct 94 may extend at an angle almost one hundred eighty degrees relative to the left internal jugular vein 92*b*, the angle of the distal portion 30 may facilitate orienting the distal tip 35 "backwards" towards the ostium of the thoracic duct 94.

Once the distal tip 35 is placed within the ostium of the thoracic duct 94, the catheter 10 may be retracted or otherwise manipulated to direct the distal portion 30 further into the thoracic duct 94. For example, if the catheter 10 is to be introduced into the left internal jugular vein 92*b*, as shown in FIG. 5, the length of the catheter 10 may be substantially shorter than most catheters, thereby providing a more direct relationship of movement between the proximal end 22 and the distal portion 30 since the catheter 10 is less likely to twist, compress, stretch, and the like between the proximal end 22 and the distal portion 30.

If the catheter 10 is manipulated to place the distal tip 35 at the ostium of the thoracic duct 94, the catheter 10 may simply be retracted (e.g., upwardly) to pull the distal tip 35 up into the thoracic duct 94, e.g., as shown in FIG. 6. In an exemplary embodiment, the distal portion 30 may pass through the terminal valve 95*a* of the thoracic duct 94 until the balloon 50 is positioned between the terminal valve 95*a* and the next valve 95*b* within the thoracic duct 94. The balloon 50 may then be inflated to engage the wall of the thoracic duct 94 and substantially seal and/or isolate the thoracic duct 94 from the veins 92.

Optionally, navigation to the thoracic duct 94 may be aided using external imaging, such as ultrasound imaging. For example, as described elsewhere herein, the distal portion 30 of the catheter 10 may include one or more echogenic features, which may facilitate identification and monitoring the balloon 50 and/or the distal tip 35. Because the thoracic duct 94 is located near the surface, i.e., close to the patient's skin, an ultrasound imaging device placed on or near the patient's skin may provide high resolution visualization of the region including the thoracic duct 94 and adjacent veins 92 to facilitate monitoring the distal portion 30 until the distal tip 35 and balloon 50 are positioned as desired.

In addition or alternatively, tactile feedback and/or manipulation may be used to facilitate positioning the distal portion 30. For example, given the close proximity of the thoracic duct 94 and neighboring veins 92 to the skin, it may be possible to feel the catheter 10 by placing the user's fingers on the patient's overlying skin and pressing against the skin and intervening tissues. Such pressure may also be used to physically manipulate the distal portion 30, e.g., in addition to manipulation of the proximal end 22, to direct the distal tip 35 into the thoracic duct 94.

In addition or alternatively, other imaging may be used, such as fluoroscopy, MRI, CT, and/or direct visualization, e.g., using an imaging element carried on the distal portion 30 of the catheter 10. Exemplary imaging elements and methods for using them are disclosed in U.S. Publication Nos. 2011/0034790, 2007/0015964, 2006/0084839, and 2004/0097788, the entire disclosures of which are expressly incorporated by reference herein.

Optionally, additional methods may be used to facilitate introducing the distal tip 35 and balloon 50 through the terminal valve 95*a*, e.g., instead of simply pushing the distal tip 35 through the valve 95*a*. For example, the terminal valve 95*a* may be monitored using external imaging or otherwise monitored to coordinate timing of movement of the terminal valve 95*a* with physiological events, e.g., heart rate, and the like, until the terminal valve 95*a* naturally opens, whereupon the distal tip 35 may be advanced through the open valve 95*a* into the thoracic duct 94. Alternatively, the user may trigger opening of the terminal valve 95*a*, e.g., by increasing lymph within the patient's body, for example, by squeezing tissue in the arm or leg.

In another alternative, a negative pressure may be created within the junction, e.g., by aspirating into the catheter 10 or otherwise, with the resulting vacuum causing the terminal valve 95*a* to open and allow the distal tip 35 to be advanced into the thoracic duct 94. In other alternatives, the user may simply periodically probe the terminal valve 95*a* by gently advancing the distal tip 35 against the valve 95*a* and/or by rotating the catheter 10 to screw the distal tip 35 through the valve 95*a*. Further alternatively, the balloon 50 (or other distal expandable member) may be at least partially expanded to assist in centering the distal tip 35 in or near the ostium in order to more easily cross the valve 95*a*.

In yet another alternative, a helical tip member (not shown) may be provided on the distal portion 30 that extends from the distal tip 35, which may be rotated to guide the distal tip 35 through the terminal valve 95*a*. In these alternatives, the distal portion 30 may pass through the terminal valve 95*a* until the balloon 50 is positioned between the terminal valve 95*a* and the next valve 95*b* within the thoracic duct 94. The balloon 50 may then be inflated to engage the wall of the thoracic duct 94 and substantially seal and/or isolate the thoracic duct 94 from the veins 92.

With the balloon 50 expanded to substantially isolate the thoracic duct 94, fluid may be aspirated into the lumen 26 of the catheter 10 and collected, e.g., as described elsewhere herein, fluid may be delivered into the thoracic duct 94, and/or other desired procedures may be performed via the thoracic duct 94.

Figure 4D:
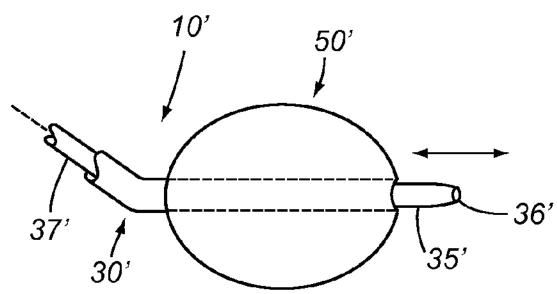
FIG. 4D is a detail of another alternative embodiment of a retractable/advanceable distal tip that may be provided on an apparatus, such as that shown in FIGS. 1-2B.
Figure 4C:
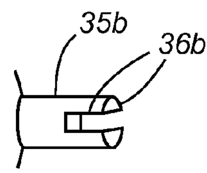

In an alternative embodiment, shown in FIG. 4D, the catheter 10' may include a movable distal tip 35,' which may be directed axially closer to or away from the balloon 50.' For example, the balloon 50' may be attached to the distal end of an outer tubular member 30,' and an inner tubular member 37' may extend through the outer tubular member 30' and the balloon 50,' and terminate in the distal tip 35.' Thus, movement of the inner tubular member 37' relative to the outer tubular member 30' may move the distal tip 35' relative to the balloon 50.' In this alternative, the balloon 50' may serve to substantially center the distal tip 35' relative to the valve(s) 95 within the thoracic duct 94 (not shown in FIG. 4D), e.g., such that the distal tip 35' may be advanced or retracted as desired relative to the valve(s) 95 to facilitate access, removal of fluid, and/or performing other procedures within the thoracic duct 94.

Optionally, the suction pressure used to aspirate lymph within the thoracic duct 94 may be adjusted, e.g., to substantially match the individual patient's maximum lymph flow. If the patient lymph flow changes over time, this method anticipates adjustment of pressure over time, both decreasing suction pressure over time, and increasing suction pressure over time, as desired.

In another option, fluids or other substances may be infused into the thoracic duct 94 or vein via the catheter 10, if desired. For example, one or more of the following may be infused: blood contaminated lymph, lymph with greater concentrations of desired substances, and the like.

In another embodiment (not shown), the catheter may include a distal end and balloon sized to be introduced into the thoracic duct. For example, the distal end may be advanced beyond a valve in the thoracic duct such that the balloon may be inflated beyond the valve. In addition or alternatively, the catheter may include one or more other features for securing and/or sealing distal to a valve, including one or more compliant rings, radial filaments/brushes, and/or other passive fixation devices (not shown) that may at least partially resist retraction or avoid spontaneous dislodgement of the catheter during use. In addition or alternatively, active fixation, such as suction, may be used to substantially fix the distal end of the catheter at a desired location, e.g., within the thoracic duct.

Figure 7:
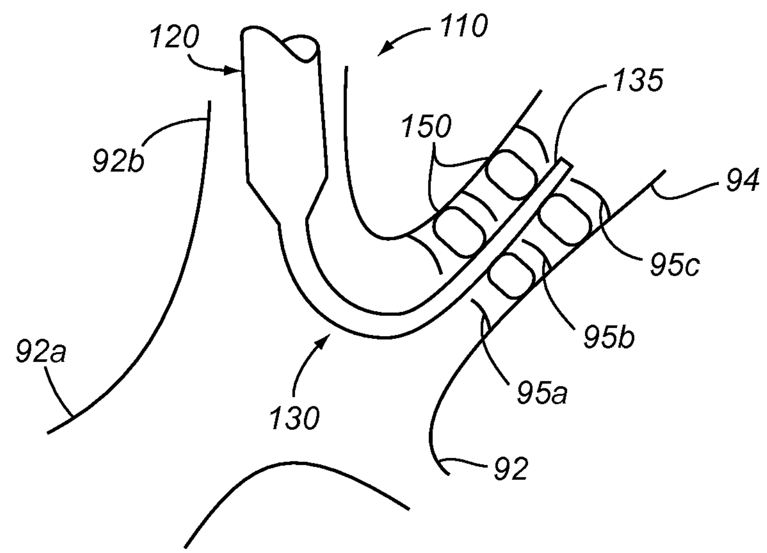
FIG. 7 is a detail of a patient's body, showing a distal portion of another exemplary embodiment of an apparatus with a pair of balloons expanded within a thoracic duct of the patient on either side of a valve within the thoracic duct.

Turning to FIG. 7, another embodiment of a catheter 110 is shown that includes a pair of balloons 150 spaced apart axially from one another on a distal portion 130 of the catheter 130. The balloons 150 may communicate with a single inflation lumen (not shown) such that the balloons 150 may be inflated and/or collapsed substantially simultaneously. Alternatively, the balloons 150 may communicate with separate inflation lumens (also not shown) such that the balloons 150 may be inflated and/or collapsed independently of one another.

As shown in FIG. 7, a distal tip 135 of the catheter 110 may be introduced into the thoracic duct 94 until the balloons 150 pass beyond the terminal valve 95*a*. Optionally, as shown, the balloons 150 may be spaced apart sufficiently from one another such that the balloons may be provided on either side of the next valve 95*b* within the thoracic duct 94. Such an arrangement of balloons 150 may provide enhanced stability for the distal portion 130 and/or improved sealing of the thoracic duct 94.

Optionally, the balloons 150 may be configured such that the balloons 150 may be positioned with a second or next valve 95*b* located between the balloons 150 and a third valve 95*c* beyond the balloons 150. When the balloons 150 are inflated, they may squeeze or otherwise engage the next valve 95*b* to enhance sealing of the thoracic duct 94 using the next valve 95*b* in addition to the balloons 150 engaging the wall of the thoracic duct 94. In another option, the balloons 150 may be positioned on either side of the terminal valve 95*a* (not shown) such that the proximal balloon engages the ostium of the thoracic duct 94 outside the terminal valve 95*a*, which may reduce the risk of blood entering the thoracic duct 94 from the veins 92. Further alternatively, the balloons 150 may be slidably disposed relative to one another (not shown) such that they may be brought together or moved apart, e.g., to capture and/or release a valve positioned between them. Further alternatively, one or more balloons may include different surface properties, e.g. a lubricious distal surface (e.g., using a hydrophilic coating, lubrication, surface features, and the like), e.g., to facilitate valve crossing and a less lubricious proximal surface to, e.g. to decrease the chance of inadvertent removal.

Figure 8:
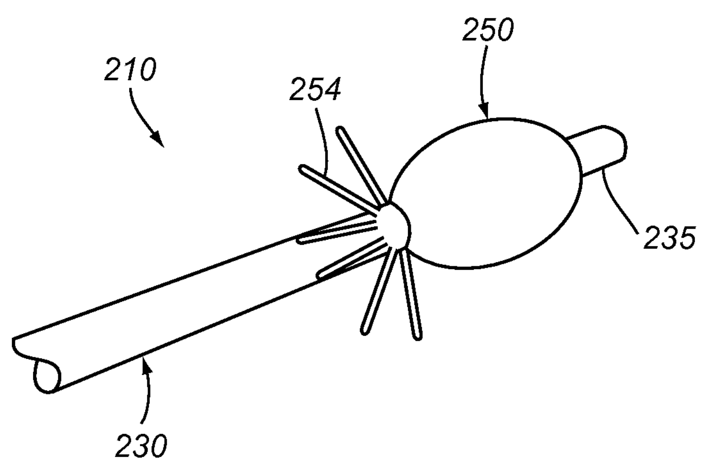
FIG. 8 is a detail showing a distal portion of another embodiment of a catheter including a plurality of expandable tines adjacent a balloon for anchoring the distal portion relative to a thoracic duct.

Turning to FIG. 8, still another embodiment of a catheter 210 is shown that includes a plurality of tines 254 on the distal portion 230 adjacent the balloon 250. The tines 254 may be biased to expand outwardly, but may be compressible inwardly, e.g., using an external sleeve or other constraint (not shown), which may be removed, e.g., after positioning the balloon 250 at a desired position within a thoracic duct (also not shown). When the tines 254 are deployed, they may engage the wall of the thoracic duct to anchor the distal portion 230 to prevent movement even if the balloon 250 is collapsed. The tines 254 may include substantially blunt free ends to engage the thoracic duct without penetrating or damaging the wall, or may include sharpened tips and/or barbs (not shown), which may be substantially permanently or indefinitely engage the wall of the thoracic duct. Thus, this embodiment may be used to secure the catheter 210 substantially indefinitely, e.g., for a long-term implant that is used to intermittently isolate the thoracic duct by expanding the balloon 250, e.g., to collect lymph. When not needed, the balloon 250 may be collapsed allowing normal function of the thoracic duct. If desired, the catheter 210 may be removed, e.g., by directing a sheath or other tubular member (not shown) into the thoracic duct to recapture and collapse the tines 254.

Figure 9A:
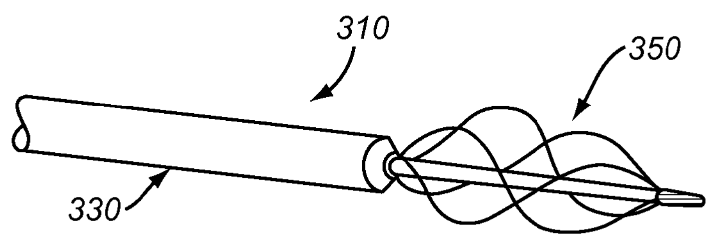
FIGS. 9A-9C are side and ends views of yet another embodiment of a catheter including a mechanically expandable member that is expandable from a collapsed configuration (FIG. 9A) to an enlarged configuration (FIGS. 9B and 9C) for isolating a thoracic duct.
Figure 9B:
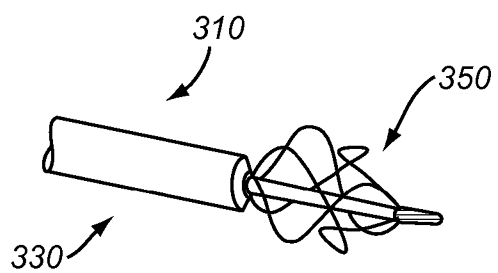
Figure 9C:
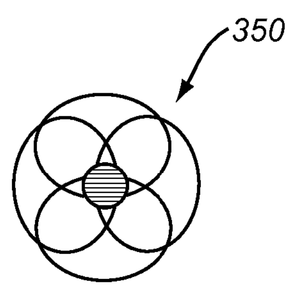

Turning to FIGS. 9A-9C, another embodiment of a catheter 310 is shown that includes an expandable frame 350 on a distal portion 330 including a set of wires or struts that may be manipulated from a proximal end (not shown) of the catheter 310. For example, an actuator on the proximal end (not shown) may be activated to direct the frame from a collapsed configuration (shown in FIG. 9A) to an enlarged configuration (shown in FIG. 9B). The size of the frame 350 may be sufficient to engage a wall of a thoracic duct when the distal portion 330 is introduced into the thoracic duct, as described elsewhere herein.

As shown in FIG. 9C, the frame 350 may carry a nonporous membrane that may be directed across the thoracic duct when the frame 350 is expanded to substantially seal the thoracic duct. Thus, the frame 350 may operate similar to the balloons described elsewhere herein, except that the frame 350 is mechanically actuated rather using fluid to inflate and collapse the balloons.

Turning to FIG. 5, the apparatus 8 may be part of a system 6 including one or more external components for performing a medical procedure, e.g., which may involve removing lymphatic fluid from the patient's body 90 via the thoracic duct 94, introducing agents or devices (not shown) into the thoracic duct 94, and/or infusing the removed lymphatic fluid, components thereof, and/or other agents into other locations within the patient's body 90. For example, one or more external devices may be provided that are coupled to the proximal end 22 of the catheter 10, e.g., for detecting, separating, collecting, and/or infusing lymphatic fluid and/or other fluids, as described in U.S. Publication No. 2011/0276023, the entire disclosure of which is expressly incorporated by reference herein. The external components may be provided integrated into a single device or may be provided as separate discrete components that are coupled to one another (e.g., along a fluid path, electrically, and/or otherwise).

In the example shown schematically in FIG. 5, the external components include a detector 60, a controller 62, a separator 64, a waste container 66, a storage container 68, and an infusion device 70. One or more of the components may include a pump or source of vacuum or pressure, e.g., for removing fluid from the patient's body and/or delivering fluid into the patient's body 90 via the catheter 10, or infusing fluids via the infusion device 70, as described further below. In alternative embodiments, one or more of the components may be omitted. For example, the catheter 10 may simply be coupled directly to the storage container 68, e.g., with or without a source of vacuum to facilitate collection of lymphatic fluid.

The detector 60 may be coupled to the proximal end 22 of the catheter 10, e.g., to the port 23*a* on the handle 23, for receiving fluids that are drawn through the lumen 26 of the catheter 10 from the inlet port 36 in the distal tip 35 (not shown in FIG. 5, see, e.g., FIGS. 2A, 2B). The detector 60 may include one or more sensors (not shown), e.g., for distinguishing between lymphatic fluid and blood. In exemplary embodiments, the sensor(s) may include one or more optical sensors (e.g., for detecting the presence of red blood cells by light transmission or reflection characteristics), chemical sensors (e.g., for detecting one or more of pH, oxygen concentration, lactate, leukocyte esterase, and the like), sensors for measuring hematocrit, electrical sensors (e.g., for measuring impedance), mechanical sensors (e.g., for detecting pressure waves, which may differ between the venous system and the thoracic duct; for flow detection, e.g., by Doppler ultrasound), filter devices sized to constituents of whole blood, and the like. In addition or alternatively, a sensor may be provided that is adapted to detect the presence of an exogenous marker introduced into the lymphatic system, such as a dye (e.g., methylene blue), an ingested marker, a fluorescent marker, and the like.

For example, a pump or other source of vacuum or pressure (not shown) within or coupled to the detector 60 may be selectively activated, e.g., by the controller 62 (or alternatively manually by a user, if desired), to remove fluid from the patient's body via the catheter 10 through the detector 60 to the separator 64. The controller 62 may automatically analyze sensor data from the sensors to identify whether the fluid is lymphatic fluid, blood, or other fluid.

For example, if the controller 62 determines that the fluid includes blood, the controller 62 may direct the fluid to the waste container 66, e.g., through the separator 64 or directly. In addition or alternatively, if the controller 62 detects the presence of a significant amount blood in the fluid (based on data from the detector 60 or otherwise) or detects a loss of seal (e.g., due a sudden pressure change in the fluid being removed via the catheter 10), the controller 62 may shut down the pump, close a shut-off valve (not shown) in the detector 60, or otherwise stop flow of fluid from the catheter 10 into the detector 60 and/or the rest of the system 6. This safety mechanism may be active, i.e., shut down automatically, or passive, i.e., merely warn the user.

In an exemplary embodiment, the separator 64 may include a valve (not shown) including an inlet 64*a* that communicates with the detector 60, a first outlet 64*b* communicating with the storage container 68, and a second outlet 64*c* communicating with the waste container 66. The valve may be selectively operable between the first and second outlets 64*b*, 64*c* by the controller 62, e.g., to direct undesired fluid, e.g., blood, to the waste container 66, and desired fluid, e.g., lymphatic fluid or components thereof, to the storage container 68. Alternatively, or in addition, the separator 64 may include one or more devices for separating various components of lymphatic fluid, including various types of cells, proteins, electrolytes, water, and/or other constituent parts of lymphatic fluid. For example, water may be substantially separated from other components in order to selectively remove excess water from a patient. As another example, pathologic cells may be selectively separated from other constituents in order to remove pathologic cells from a patient.

In an alternative embodiment, a filter (not shown) may be provided within the detector 60 or separator 64, which may clog in the presence of a predetermined number or concentration of cells, e.g., red blood cells, to prevent the fluid from being delivered into the storage container 68. In a further alternative, coagulation/clotting may be used to prevent flow in the presence of whole blood and its constituents (for example, platelets). For example, a passage through the detector 60 or other external component may be sized to clot spontaneously, a filter may be used where clotting decreases flow, and/or pro-coagulant materials may be used to augment or accelerate a clotting response. In such alternatives, the component of the system 6 designed to prevent flow may be cleanable and/or replaceable, e.g., to allow to resumption of flow after isolation of the thoracic duct 94 is reestablished.

If the controller 62 confirms that the fluid is lymphatic fluid, the controller 62 may activate the separator 64 to direct the lymphatic fluid or components of the lymphatic fluid into the storage container 68. For example, if the entire lymphatic fluid is to be collected, the separator 64 may simply divert the fluid into the storage container 68. Alternatively, it may be desirable to separate certain constituents of the removed fluid, e.g., lymphatic fluid, particular cells, proteins, and the like. For example, the separator 64 may include one or more of a mechanical filtration system, an osmotic gradient system, a concentration gradient system, a centrifuge, and the like to separate the desired components from the rest of the fluid. Once separated, the desired components may be delivered to the storage container 68, while the rest of the fluid is delivered to the waste container 66.

Optionally, the controller 62 or other components of the system 6 may monitor the flow to keep track of the amount of fluid extracted and/or to stop after a predetermined amount of fluid is extracted. In addition or alternatively, the controller 62 may operate the pump, vacuum source, valve, and/or other components of the system 6 periodically or otherwise intermittently, e.g., to allow reaccumulation of fluid within the lymphatic vessels.

In certain cases, it may be desirable to re-infuse all or a portion of the lymphatic fluid removed, for example, all cells and/or proteins (e.g., discard fluid and retain the useful constituents of lymph), only a certain portion of removed cells and/or proteins, (e.g., discard harmful constituents and retain useful constituent), and/or other constituents of the removed lymphatic fluid. One approach may be simply to retain an initial volume of removed fluid that may have a higher concentration of cells, proteins, and the like compared to the subsequent volume removed. For example, there may be a relatively small initial volume of lymphatic fluid in the vessels that, upon sustained drainage, may be repleted with interstitial fluid having relatively few cells. Alternatively, filtration, separation, or other methods may be used to create a desirable portion for reinfusion.

For example, as shown in FIG. 5, an infusion catheter 70 may be provided that includes a proximal end 70*a* coupled to the storage container 68, and a distal end 70*b* sized for delivering the stored fluid into the patient's body 90.

In addition to the trans-venous approaches described elsewhere herein, it may also be possible to directly cannulate a lymphatic vessel and/or associated lymph node in order to access the lymphatic system using any of the systems and methods herein.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

We claim:

1. A method for performing a medical procedure within a patient's body, the body comprising a thoracic duct including a terminal valve and an ostium communicating with a patient's venous system of the patient's body, comprising:

introducing a distal portion of a tubular member through the patient's venous system into a body lumen adjacent the terminal valve and ostium of the thoracic duct, the distal portion biased to a curvilinear configuration;

manipulating the tubular member until a distal tip of the distal portion enters the ostium of the thoracic duct;

further manipulating the tubular member to direct the distal portion into the thoracic duct until an expandable member on the distal portion passes through the terminal valve;

expanding the expandable member within the thoracic duct beyond the terminal valve to substantially isolate the thoracic duct from the body lumen; and performing a medical procedure via the thoracic duct, wherein the expandable member comprises a first balloon, the method further comprising expanding a second balloon on the distal portion adjacent the first balloon.

2. The method of claim 1, wherein the medical procedure comprises removing lymphatic fluid from the thoracic duct through a lumen of the tubular member.

3. The method of claim 1, wherein the medical procedure comprises introducing one or more agents into the thoracic duct through a lumen of the tubular member.

4. The method of claim 1, wherein the expandable member is expanded within a region of the thoracic duct between two valves.

5. The method of claim 4, wherein the expandable member substantially fills the region between the two valves when expanded.

6. The method of claim 1, wherein the first and second balloons are expanded such that either the terminal valve or a next valve adjacent to the terminal valve in the thoracic duct is captured between the first and second balloons.

7. The method of claim 1, further comprising moving one of the first and second balloons relative to the other.

8. The method of claim 7, wherein one of the first and second balloons is moved relative to the other to capture either the terminal valve or a next valve adjacent to the terminal valve between the first and second balloons.

9. The method of claim 1, wherein the first balloon is expanded within the thoracic duct adjacent the terminal valve and wherein the second balloon is expanded to engage the ostium outside the terminal valve.

10. The method of claim 1, wherein the first balloon is expanded within the thoracic duct between the terminal valve and a next valve adjacent to the terminal valve and wherein the second balloon is expanded beyond the next valve.

11. The method of claim 1, wherein the distal portion is supported by a stylet positioned through a proximal portion of the tubular member into the distal portion when the distal portion is introduced into the body lumen.

12. The method of claim 11, further comprising:

removing the stylet to release the distal portion within the body lumen, wherein the distal portion returns towards the curvilinear configuration before the tubular member is manipulated to direct the distal tip into the ostium of the thoracic duct.

13. The method of claim 11, further comprising positioning the stylet into the distal portion before introducing the distal portion into the body lumen such that the stylet directs the distal portion from its curvilinear configuration to a less curved or substantially straight configuration.

14. The method of claim 11, further comprising replacing the stylet with one or more shaped stylets before further manipulating the tubular member to direct the distal portion into the thoracic duct.

15. The method of claim 1, wherein expanding the expandable member comprises expanding the first balloon on the distal portion within the thoracic duct between the terminal valve and a next valve within the thoracic duct.

16. The method of claim 15, further comprising expanding the second balloon on the distal portion within the thoracic duct distally beyond the next valve.

17. A method for performing a medical procedure within a patient's body, the body comprising a thoracic duct including a terminal valve and an ostium communicating with a patient's venous system of the patient's body, comprising:

introducing a distal portion of a tubular member through the patient's venous system into a body lumen adjacent the terminal valve and ostium of the thoracic duct, the distal portion biased to a curvilinear configuration;

manipulating the tubular member until a distal tip of the distal portion enters the ostium of the thoracic duct;

further manipulating the tubular member to direct the distal portion into the thoracic duct until an expandable member on the distal portion passes through the terminal valve;

expanding the expandable member within the thoracic duct beyond the terminal valve to substantially isolate the thoracic duct from the body lumen; and performing a medical procedure via the thoracic duct, wherein the distal portion of the tubular member has a curvilinear shape in a relaxed state and terminates in the distal tip, and wherein a proximal portion of the tubular member comprises a distal end including a transition that tapers such that the distal portion has a smaller outer diameter along its length than the proximal portion;

wherein introducing the distal portion of the tubular member comprises:

introducing the distal portion of the tubular member into a patient's vasculature via a percutaneous access site in the patient's left internal jugular vein;

advancing the tubular member until the distal portion is disposed near a junction of the left internal jugular vein and the patient's left subclavian vein and the proximal portion is disposed through the access site and in the left internal jugular vein; and manipulating the tubular member to orient the distal tip towards the thoracic duct;

wherein further manipulating the tubular member comprises retracting the tubular member to direct the distal tip and the expandable member into the thoracic duct beyond a terminal valve of the thoracic duct; and wherein expanding the expandable member comprises:

expanding a first balloon on the distal portion within the thoracic duct between the terminal valve and a next valve within the thoracic duct; and expanding a second balloon on the distal portion within the thoracic duct distally beyond the next valve.

18. The method of claim 17, wherein the distal portion is at least partially straightened or otherwise supported while the tubular member is introduced into the patient's vasculature and the tubular member is advanced until the distal portion is disposed within the junction of the left internal jugular vein and the left subclavian vein.

19. The method of claim 17, wherein the first and second balloons engage opposite sides of the next valve when expanded to enhance sealing the thoracic duct.

* * * * *